US00PP19817P2

(12) United States Plant Patent
Yates

(10) Patent No.: US PP19,817 P2
(45) Date of Patent: Mar. 10, 2009

(54) ***BEGONIA* PLANT NAMED 'YAGANCE'**

(50) Latin Name: *Begonia hybrida*
Varietal Denomination: Yagance

(76) Inventor: Frederic C. Yates, Holmes Chapel Rd., Somerford, Congleton, Cheshire (GB), CW12 4SP ( * ) Notice: Subject to any disclaimer, the term of this patent is extended or adjusted under 35 U.S.C. 154(b) by 0 days.

(21) Appl. No.: 12/008,332

(22) Filed: Jan. 10, 2008

(51) Int. Cl.
*A01H 5/00* (2006.01)

(52) U.S. Cl. ..... Plt./343
(58) Field of Classification Search ..... Plt./343
See application file for complete search history.

*Primary Examiner*—Annette H. Para
*Assistant Examiner*—S. B McCormick Ewoldt
(74) *Attorney, Agent, or Firm*—Penny J. Aguirre

(57) ABSTRACT

A new cultivar of *Begonia,* 'Yagance', characterized by its pink and white bi-colored flowers, its compact, freely branched, and spreading to pendulant plant habit and its vigorous growth habit.

2 Drawing Sheets

RELATED APPLICATIONS

This application is co-pending with U.S. Plant patent application Ser. No. 12/008,311 filed for a cultivar derived from the same parentage entitled *Begonia* Plant Named 'Yamance'.

Botanical classification: *Begonia hybrida.*

Cultivar designation: 'Yagance'.

BACKGROUND OF THE INVENTION

The present invention relates to a new and distinct cultivar of *Begonia* plant of hybrid origin, botanically known as *Begonia* 'Yagance' and will be referred to hereafter by its cultivar name, 'Yagance'.

The new cultivar was derived from a controlled breeding program conducted by the inventor at his nursery in Congleton, Cheshire, U. K. The overall purpose of the breeding program is to make selections of *Begonia* plants with compact plant habits suitable for basket and patio containers. 'Yagance' was selected as a a single unique plant in 2005 and derived from a cross made between an unnamed proprietary plant of hybrid *Begonia* as the female parent plant and *Begonia boliviensis* 'Yabos' (U.S. Plant patent application Ser. No. 11/445,753) as the male parent.

Asexual reproduction of the new cultivar was first accomplished by terminal stem cuttings in Congleton, Cheshire, U. K. in 2005 by the inventor. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'Yagance' as a new and distinct cultivar of *Begonia.*

1. 'Yagance' exhibits single bi-color flowers with pink outer tepals and white inner tepals.
2. 'Yagance' readily produces side shoots.
3. 'Yagance' exhibits a compact, spreading to pendulous plant habit.
4. 'Yagance' has a vigorous growth habit.

In comparison, the unnamed female parent of 'Yagance' differs from 'Yagance' in having double flowers and the male parent, 'Yabos', differs from 'Yagance' in having red-orange flowers. 'Yamance', its sibling selection, differs from 'Yagance' in having apricot pink flowers. 'Yagance' can also be compared to 'Bonfire' (U.S. Plant No. 15,108), which differs from 'Yagance' in having flowers that are red and not bi-color.

BRIEF DESCRIPTION OF THE DRAWING

The accompanying colored photographs illustrate the overall appearance and distinct characteristics of the new *Begonia.* The photographs were taken in September of a plant approximately 6 months in age as grown in a two-liter container in Swavesey, Campbridgeshire, U.K.

The photograph in FIG. 1 provides a side view of 'Yagance' in bloom.

Figure 1:
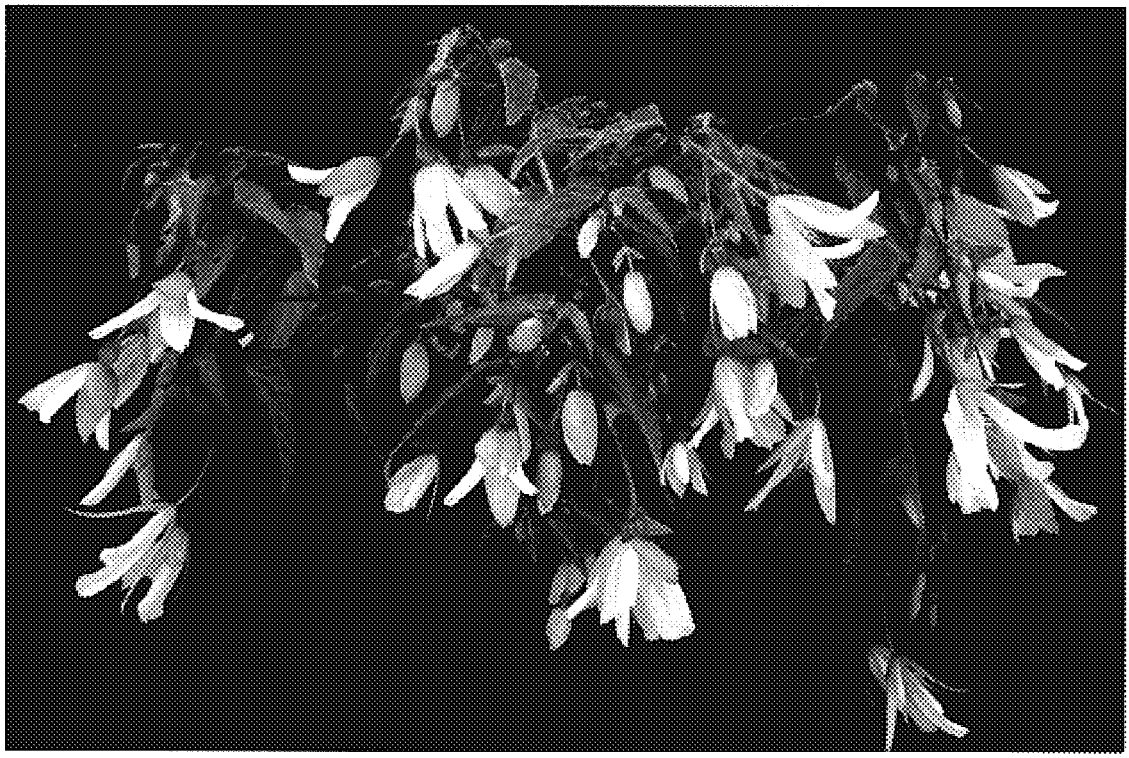
Figure 2:
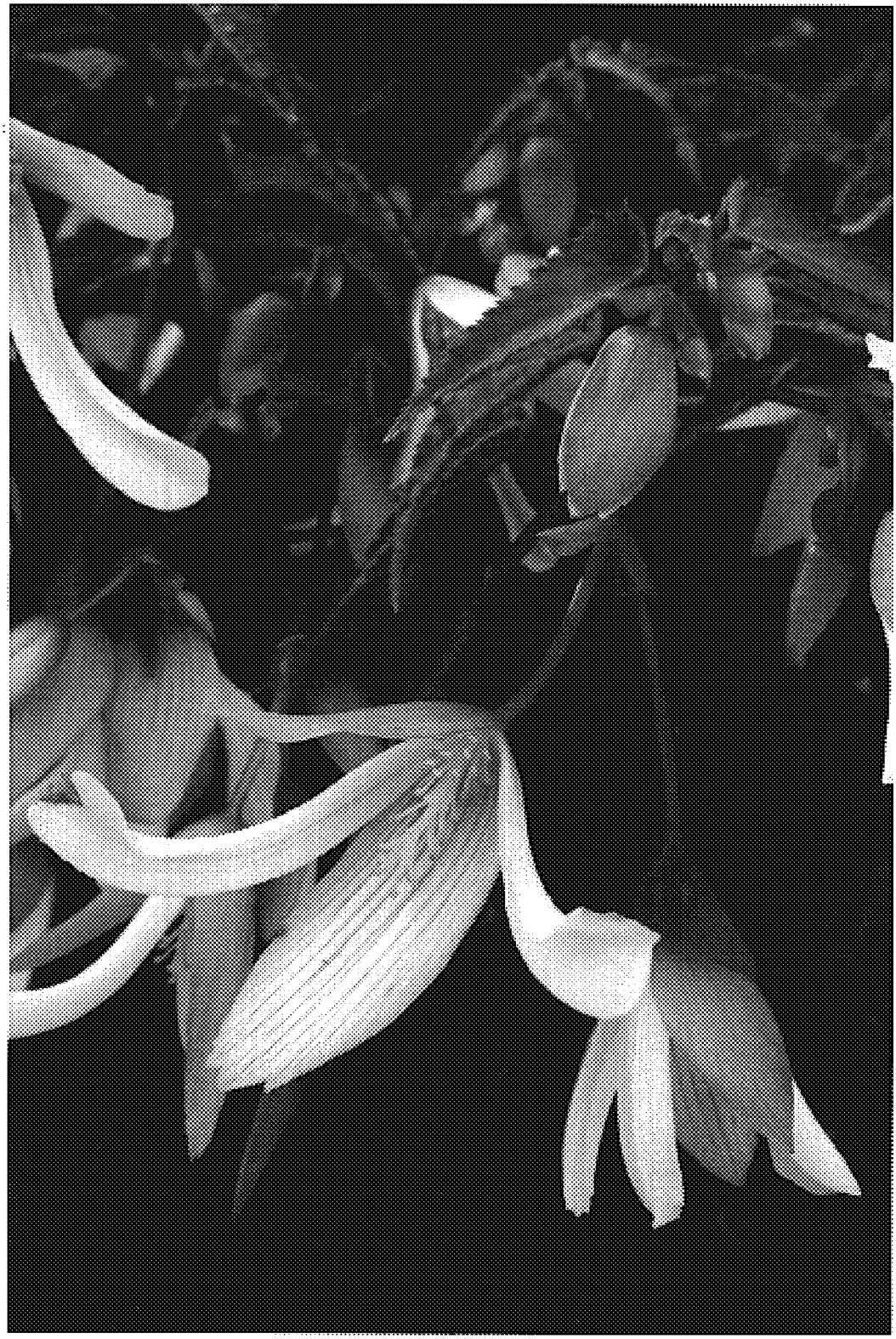

The photograph in FIG. 2 provides a close-up view of the flowers of 'Yagance'. The colors in the photographs are as close as possible with the photographic and printing technology utilized. The color values cited in the detailed botanical description accurately describe the colors of the new *Begonia.*

DETAILED BOTANICAL DESCRIPTION OF THE PLANT

The following is a detailed description of plants of the new cultivar approximately 6 months in age as grown in two-liter containers under greenhouse conditions with ambient light in Congleton, Cheshire, U. K. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General Plant Characteristics:

*Plant type.*—Deciduous tuberous perennial, grown primarily for use in baskets and containers.

*Plant habit.*—Compact, spreading becoming pendulous.

*Flowering period.*—From April to November.

*Height and spread.*—Reaches about 26 cm in height and about 44 cm in spread.

*Cold hardiness.*—U.S.D.A. Zone 10.

*Culture.*—Grows in any commercial soil or growing media, 12 hours of light is needed for production in the winter months.

*Diseases and Pests.*—No susceptibility or resistance to diseases or pests has been observed.

*Root description.*—Fleshy to fibrous with tubers produced for over-wintering.

*Tubers.*—Unevenly globose in shape with upper surface often flattened or slightly depressed in the center, average of 80 mm in diameter (larger on older plants), surface is somewhat lobed and slightly corky, color between 199C and 199D.

Growth and Propagation:

*Growth rate.*—Vigorous.

*Propagation.*—Terminal stem cuttings.

*Time required for root development.*—10 to 14 days at 22° C.

*Time required for root development.*—5 to 8 weeks to reach commercial size.

Stem Description:

*Stem size.*—Average of 27 cm in length and 1 cm in width with lateral branches about 4 mm in width.

*Stem shape.*—Round, solid.

*Stem color.*—199A when shaded and 183A in full sun.

*Stem surface.*—Smooth, glabrous but weakly glaucous, lenticels absent.

*Internode length.*—Average of 2 cm.

*Branching habit.*—Freely branched on non-flowering nodes.

*Branching angle at emergence.*—About 45°.

Foliage Description:

*Leaf shape.*—Lanceolate, asymmetric with one side wider than the other.

*Leaf division,*—Simple.

*Leaf base.*—Rounded on narrower side, cordate on wider side.

*Leaf apex.*—Acuminate.

*Leaf venation.*—Pinnate, color upper surface; closest to 147B, color lower surface; closest to 195B.

*Leaf margins.*—Serrate with sharp bristles emerging from tips of the teeth.

*Leaf attachment.*—Petiolate.

*Leaf arrangement.*—Alternate.

*Leaf surface.*—Upper surface; sparsely finely pubescent, lower surface; sparsely pubescent.

*Leaf color.*—Upper surface; closest to 147A, lower surface; 147C near veins and tinged with 175B between veins.

*Leaf size.*—Average of 7.5 cm in length and 2.8 cm in width.

*Leaf fragrance.*—None.

*Petioles.*—About 1.2 cm in length and 2 mm in width, surface is very sparsely to moderately pubescent with simple hairs, color 178D.

*Stipules.*—Ovate-triangular in shape, nearest 179B in color and rapidly becoming dry and papery, about 4 mm in length and 3 mm in width.

Flower Description:

*Inflorescence type.*—2 to 3 flowered cyme produced sequentially in the axils of the upper leaves, monoecious with terminal male flowers developing before the lateral female flowers.

*Flower persistence.*—Self-cleaning.

*Flower type.*—Single, funnel formed with un-fused tepals.

*Flower fragrance.*—None.

*Peduncles.*—30 mm in length and 2 mm in width, 180B in color, surface is glabrous.

*Bract.*—Typically 2, present at base of cyme, broadly ovate to round in shape and curled around pedicel, shallowly bifid apex, about 8 mm in length and width, 180C in color, margin is finely serrated on half towards apex.

Male Flowers:

*Pedicels.*—About 2.7 cm in length and 2 mm in width, 41A in color, surface is glabrous.

*Flower buds.*—Flattened ovoid in shape, about 2.6 cm in length and 1.3 mm in width, 43D in color.

*Flower size.*—About 3.5 cm in length and 5.5 cm in width.

*Flower aspect.*—Hanging with flared unfused tepals.

*Outer tepals.*—2, ovate-elliptic in shape, obtuse apex, rounded base, average of 3.9 cm in length and 1.7 mm in width, glabrous and smooth surface, entire margin except apex is serrated, outer surface is 43D in color (slightly paler), inner surface is 159D with veins 43D.

*Inner tepals.*—2, narrow obovate to linear in shape recurving slightly towards apex, obtuse-truncate apex, narrow cuneate base, average of 4.5 cm in length and 1.4 cm in width, glabrous and smooth surface, entire margin, outer surface is 155B in color with a slight tinge of 43D in the center of basal portion, inner surface is 155B.

*Stamens.*—Connate below forming a tube, about 2 cm in overall length with tube portion 1.3 cm in length and 1.3 mm in width, 12C in color, numerous in number.

*Filaments.*—About 3 mm in length and 0.5 mm in width, 163D in color.

*Anthers.*—Broadly elliptic in shape, about 1 mm in length and <1 mm in width, 163A in color.

*Pollen.*—Abundant, 8C in color.

Female Flowers:

*Pedicels.*—About 3.4 cm in length and 1.5 mm in width, 41A in color, glabrous surface.

*Flower buds.*—Flattened ovate in shape, about 1.9 cm in length and 8 mm in width, closest to 43D in color.

*Flower aspect.*—Hanging with flared unfused tepals.

*Flower size.*—About 2.7 cm in length and 3.2 cm in width.

*Outer tepals.*—2, ovate in shape, acute apex, rounded base, average of 2.9 cm in length and 1.2 mm in width, glabrous and smooth surface, entire margin, outer surface is 43D, inner surface is 159D veined with 43A.

*Inner tepals.*—3, narrow-obovate to linear in shape recurving slightly towards apex, obtuse-truncate apex, narrow cuneate base, average of 3.2 cm in length and 1.1 cm in width, glabrous and smooth surface, entire margin, outer surface is 155B and weakly suffused with 43D in center of basal half, inner surface is 155B and very weakly suffused with 43D in center of basal half.

*Styles.*—3, cylindrical, connate for basal 1 mm, about 5 mm in length and 1 mm in width, 12B in color.

*Stigmas.*—Bifid in shape, lobes about 7 mm in length and <1 mm in width, 12A in color.

*Ovaries.*—Inferior, triangular in cross section with unequal wings, about 1 cm in length and 6 mm in width (excluding wings), color is 180B changing to 42B at apex of wings.

*Seed.*—Very numerous, ovate-elliptic in shape, to small to measure, N167B in color.

It is claimed:

1. A new and distinct cultivar of *Begonia* plant named 'Yagance' as herein illustrated and described.

* * * * *